United States Patent [19]
Park et al.

[11] Patent Number: 6,128,534
[45] Date of Patent: Oct. 3, 2000

[54] IMPLANTABLE CARDIAC STIMULATION DEVICE AND METHOD FOR VARYING PACING PARAMETERS TO MIMIC CIRCADIAN CYCLES

[75] Inventors: Euljoon Park, Stevenson Ranch; Gene A. Bornzin, Simi Valley; Joseph J. Florio, La Canada; Kerry Bradley, Pasadena, all of Calif.; William Gibb, Princeton, N.J.

[73] Assignee: Pacesetter, Inc., Sylmar, Calif.

[21] Appl. No.: 09/097,726

[22] Filed: Jun. 16, 1998

[51] Int. Cl.$^7$ .................................................. A61N 1/365
[52] U.S. Cl. ................................................ 607/17; 607/25
[58] Field of Search ........................... 607/4–7, 9, 17–26

[56] References Cited

U.S. PATENT DOCUMENTS

| | | |
|---|---|---|
| 4,922,930 | 5/1990 | Adkins et al. . |
| 4,945,909 | 8/1990 | Fearnot et al. . |
| 5,143,065 | 9/1992 | Adkins et al. . |
| 5,300,092 | 4/1994 | Schaldach . |
| 5,476,483 | 12/1995 | Bornzin et al. . |
| 5,514,162 | 5/1996 | Bornzin et al. . |
| 5,861,011 | 1/1999 | Stoop .......................................... 607/25 |

OTHER PUBLICATIONS

Bronzin, et al "Adjusting Heart Rate During Sleep Using Activity Variance" pp. 1933–1938, PACE, vol. 17, Nov. 1994, Pt. II.

Morris–Thurgood, et. al "A Rate Responsive Pacemaker that Physiologycally Reduces Pacing Rates at Rest" pp. 1928–1932, PACE vol. 17, Nov. 1994, Pt. II.

Djordjevic, et al. "Circadian Variations of Heart Rate and STIM–T Interval: Adaptation for Nighttime Pacing" pp. 1757–1762, PACE vol. 12, Nov. 1989.

Chew, et al "Overnight Heart Rate and Cardiac Function in Patients with Dual Chamber Pacemakers" pp. 822–828, PACE vol. 19, May 1996.

*Primary Examiner*—William E. Kamm
*Assistant Examiner*—George R. Evanisko

[57] ABSTRACT

Provided herein are methods and apparatus for automatically adjusting pacing parameters in implantable programmable stimulation devices, such as rate-responsive pacemakers and cardioverter defibrillators. The methods and apparatus provide a circadian varying pacing parameter (e.g., pacing rate, AV Delay, etc.) that very closely mimics the natural diurnal fluctuations of a patient's heart. Using physiological parameters that vary diurnally (e.g., minute ventilation and/or activity variance, etc.), a circadian-base value is derived. In the preferred embodiments, the physiological measurements are used to derive a histogram from which certain characteristic values are determined. These physiological characteristic values, along with the predetermined characteristic rates, automatically and periodically determine a transfer function from which the patient's appropriate circadian base rate is derived. Further contemplated herein are the use of more than one physiological parameter to derive a final circadian base rate, and stimulation devices employing these methods.

47 Claims, 5 Drawing Sheets

IMPLANTABLE CARDIAC STIMULATION DEVICE AND METHOD FOR VARYING PACING PARAMETERS TO MIMIC CIRCADIAN CYCLES

FIELD OF THE INVENTION

This invention relates to implantable programmable stimulation devices (such as rate-responsive pacemakers, cardioverters and defibrillators) having an improved method and system for automatically adjust pacing parameters to mimic natural diurnal fluctuations. According to the present invention, circadian adjustments to the desired pacing parameter are automatically derived using a sensor which senses a physiological parameter having circadian variations.

BACKGROUND OF THE INVENTION

In response to the adverse effects of the fixed rate pacing intrinsic to early implantable pacemakers, "rate-responsive" pacemakers were developed which can automatically adjust the patient's heart rate in accordance with metabolic demands. Similarly, implantable cardioverter defibrillators (ICDs) that include pacing circuitry also may, and preferably do, pace in a rate-responsive manner. An implanted rate-responsive pacemaker (or ICD having rate-responsive pacing capabilities) typically operates to maintain a predetermined minimum heart rate when the patient is engaged in physical activity at or below a threshold level, and gradually increases the maintained heart rate in accordance with increases in physical activity until a maximum rate is reached. Thus, such rate-responsive pacemakers typically include processing circuitry that correlates measured physical activity to an appropriate heart rate. In many rate-responsive pacemakers, the minimum heart rate, maximum heart rate and the transition rates between the minimum and maximum heart rates are parameters that may be telemetrically adjusted to meet the needs of a particular patient.

Most rate-responsive pacemakers employ sensors that transduce mechanical forces associated with physical activity to determine the level of metabolic need of a patient, relying upon the clinical association of body motion with increasing levels of exercise. These activity sensors generally contain a piezoelectric transducing element which generates a measurable electrical potential when a mechanical stress resulting from physical activity is experienced by the sensor. Thus, by analyzing the signal from a piezoelectric activity sensor, a rate-responsive pacemaker can determine how frequently pacing pulses should be applied to the patient's heart.

Another physiological sensor frequently used in rate-responsive pacemakers are respiration sensors. Such sensors may be employed to measure respiratory rate (RR), tidal volume (TV) or the product of these two parameters, minute ventilation (MV). Each of these parameters increases in proportion to changes in carbon dioxide production. Minute ventilation-sensing, rate-adaptive pacing systems have been demonstrated to provide rate modulation that is closely correlated with oxygen consumption in most patients implanted with these devices. See, *CARDIAC PACING*, edited by Kenneth A. Ellenbogen, Blackwell Scientific Publications, Cambridge, Mass. (1992), page 94.

Minute ventilation is generally estimated by frequent measurements of transthoracic impedance between an intracardiac lead and the pulse generator case using a tripolar system. Transthoracic impedance increases with inspiration and decreases with expiration. Thus, by measuring the frequency of respiration-related fluctuations in impedance (correlated with respiratory rate) and the amplitude of those excursions (correlated with tidal volume), the estimated minute ventilation can be calculated. (*CARDIAC PACING*, referred to above, at page 94.)

It is well established that a myriad of physiological processes demonstrate a rhythmic variation during a twenty-four hour period. Such daily variations are referred to as circadian or diurnal variations. The intrinsic cardiac rhythmicity of both normal and diseased hearts is subject to circadian variations. For example, minimum heart rate decreases during sleep. See, Djordjevic, M. et al., "Circadian Variations of Heart Rate and STIM-T Interval: Adaptation for Nighttime Pacing," *PACE*, 12:1757–1762 (1989). While rate-responsive pacemakers are able to pace according to the presently measured metabolic need of the patient, many are set with minimum pacing rates that are not adjusted according to such circadian fluctuations. In fact some pacemakers are programmed with a single minimum pacing rate as high as 80 bpm, because the rate does not change. However, recently researchers have shown that sustaining such rates around the clock may induce cardiac performance that is consistent with heart failure. See, Chew, et al., "Overnight heart rate and cardiac function in patients with dual-chamber pacemakers," *PACE* 19:822–828 (1996).

Thus, a number of cardiac pacemakers have been developed to sense stages in a patient's circadian rhythm or activity level and to alter the output of pacing pulses in response thereto. For example, U.S. Pat. Nos. 4,922,930 and 5,143,065, both issued to Adkins et al., disclose a cardiac pacemaker which can vary the rate of pacing pulses in accordance with a wake-sleep cycle based on a model having multiple time periods. Each period has a specific duration, which periods are maintained with a real-time clock located within the pacemaker, and a predicted minimum physiologic need for the patient is correlated to each time period.

Similarly, U.S. Pat. No. 4,945,909 to Fearnot et al. discloses a pacemaker that paces at a rate defined within a range having variable upper and lower rate limits. These limits change in response to patient activity sensed by the pacemaker. U.S. Pat. No. 5,300,092 to Schaldach also discloses a cardiac pacemaker which can vary the rate of pacing pulses in response to the patient's sensed activity. U.S. Pat. No. 5,476,483 to Bornzin et al. discloses a cardiac pacemaker that varies a base pacing rate of a predetermined transfer function according to sensed activity levels, and U.S. Pat. No. 5,514,162, also issued to Bornzin et al., describes a method for automatically determining the slope of a transfer function that is used by the pacemaker to determine appropriate heart rates in accordance with metabolic demands. Each of U.S. Pat. Nos. 5,476,483 and 5,514,162 are hereby incorporated by reference, in their entirety.

These pacemakers can produce a cardiac rhythm that more closely mimics a natural rhythm than pacemakers that do not change their output in response to activity levels or to stages in a patient's circadian rhythm, but the degree to which they mimic the patient's natural rhythm varies.

Most patients would benefit, then, from a pacemaker which could vary its output to mimic a natural rhythm even more closely and reliably. Additionally, as a patient's heart or lifestyle changes over time, it would be advantageous to have a pacemaker which can vary its output in response to a patient's circadian rhythm in a manner that is selectable according to the patient's needs. Still further, it is desirable that any new methods of adjusting pacing rates to mimic circadian rhythms be easily applied to existing pacemakers having the ability to sense circadian biorhythms.

SUMMARY OF THE INVENTION

The present invention addresses the above and other needs by providing methods and apparatus for adjusting a pacing parameter of an implantable programmable stimulation device, such as a rate-responsive pacemaker and/or implantable cardioverter defibrillator (ICD), to coincide with the patient's circadian rhythm.

While the preferred embodiment is directed towards a circadian base rate, other pacing parameters are also within the scope of this invention, such as the AV Delay, the mode switching threshold, the tachycardia detection thresholds, defibrillation output amplitude, or the aggressiveness of therapy, or any pacing parameter or threshold that should be varied diurnally.

In the preferred embodiment, the methods and apparatus provided herein, provide chronotropically incompetent patients with appropriate chronotropic daytime support while allowing typical nighttime resting rates.

In preferred embodiments, the invention provides a control algorithm, for programming into and controlling the stimulation device, which algorithm automatically adjusts a pacing parameter (e.g., the base pacing rate) to model the natural circadian variation in that parameter (e.g., heart rate) using a diurnally varying sensor. Significantly, the inventors have discovered that physiological parameters that vary diurnally may be manipulated to derive an appropriate circadian varying pacing parameter, which very closely mimics natural diurnal fluctuations for that parameter.

In one embodiment, a physician or other clinician need only program an upper and a lower target value for a desired parameter (e.g., a target daytime and a target nighttime for the pacing rate) into the stimulation device. The device is then able to appropriately adjust the desired parameter as a function of the diurnally varying sensor. The transfer function is based on a histogram of the sensed physiological parameters.

It has been discovered that while activity sensors are not diurnally varying, activity variance does. Other sensors that are suitable include minute ventilation, QT interval, or other contractility sensor data, or a combination thereof.

Advantageously, when the methods and apparatus are applied to pacing rate, the present invention generates a cardiac rhythm, based upon circadian variations in heart rates, that more closely mimics the natural diurnal fluctuations of a normal sinus rhythm. In fact, the circadian base rate, described herein, constitutes over 90% of the rate change for the normal activities of daily living, and thus, this rate is more dominant in its effect on mimicking sinus rate than other, known rate-response processes.

It is thus a feature of the invention to provide an improved method of adjusting the base rate (circadian base rate) of an implantable programmable stimulation device (rate-responsive pacemaker or ICD) to more closely mimic the natural diurnal fluctuations in sinus rates, and to provide an improved stimulation device capable of employing such method. An important aspect of this invention is that it can be simply implemented and easily programmed into existing rate-responsive stimulation devices having at least one sensor for sensing a physiological parameter sensitive to circadian biorhythms.

DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

It will be appreciated by those of skill in the art that the invention described herein may be successfully employed in any programmable rate-responsive stimulation device, including without limitation pacemakers and implantable cardioverter defibrillators (ICDs), where the stimulation device includes at least one sensor capable of sensing a physiological parameter indicative of the patient's metabolic pacing needs. Thus, as used herein, references to rate-responsive pacemakers are intended to apply to all such stimulation devices.

Figure 1:
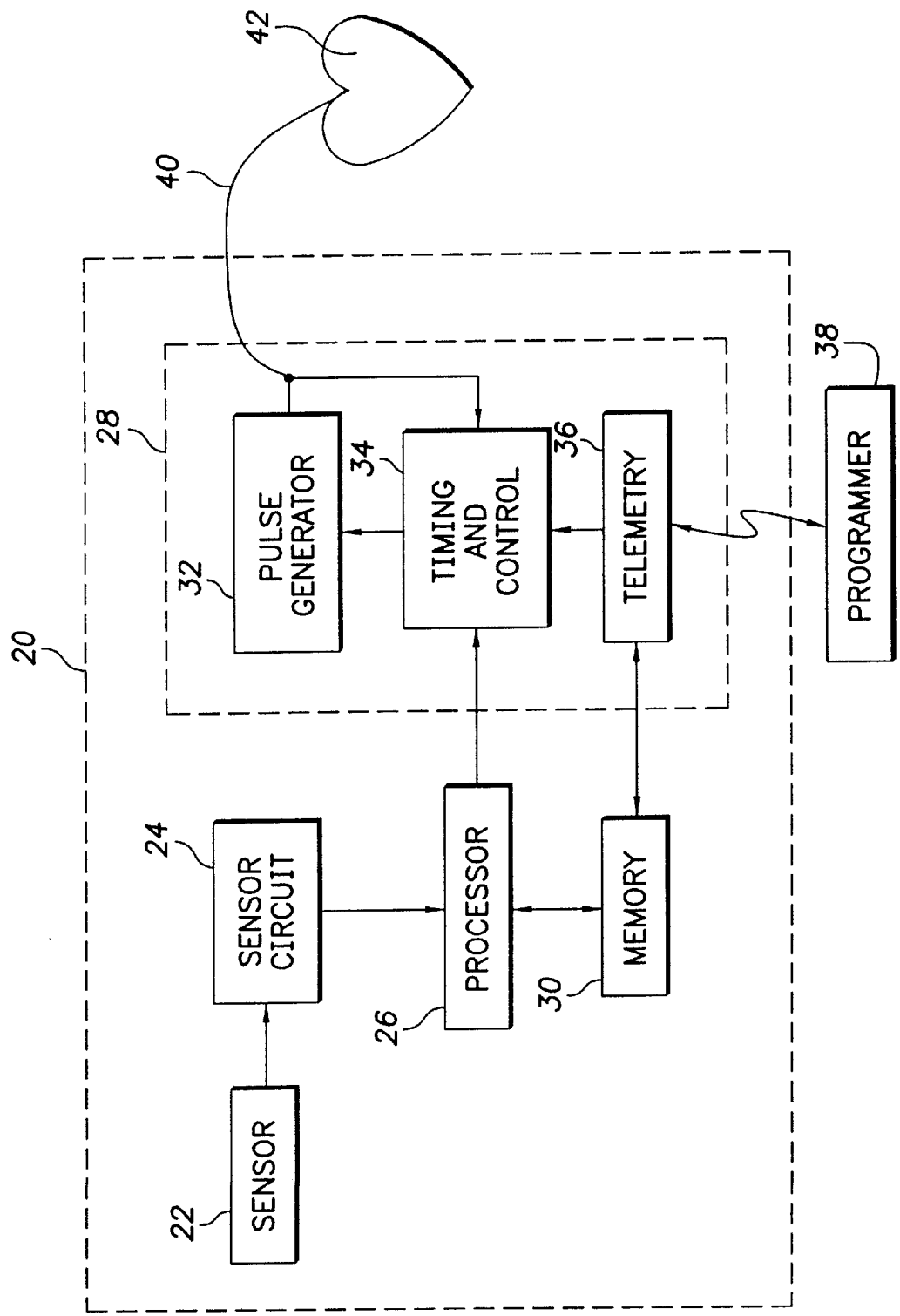
FIG. 1 shows a simplified functional block diagram of a rate-responsive pacemaker which can modulate the circadian base rate in accordance with the principles of the present invention.

Referring first to FIG. 1, a block diagram representing a rate-responsive pacemaker 20 configured in accordance with the principles of the present invention is illustrated. In many respects, the pacemaker 20 operates in a conventional manner to provide pacing pulses at a rate that comfortably meets the patient's metabolic demands. More precisely, the pacemaker 20 uses signals generated by at least one sensor 22, such as an activity sensor and/or minute ventilation sensor, to determine the extent to which the patient is engaged in physical activity—the measured level of activity or minute ventilation being used as an indicator of metabolic need.

The signals generated by the sensor 22 are initially received by a sensor circuit 24. The sensor circuit 24 initially processes the raw signals generated by the sensor 22 to provide digital sensor signals to a processor 26, which preferably includes a microprocessor (not shown). The processor 26 is additionally coupled to a pacemaker circuit 28 (which may be conventional) and a memory 30. The pacemaker circuit 28 typically includes a pulse generator circuit 32, a timing and control circuit 34 and a telemetry circuit 36, wherein the timing and control circuit 34 is coupled to the pulse generator circuit 32, the processor 26 and the telemetry circuit 36. The telemetry circuit 36, which telemetrically communicates with an external programmer 38, is coupled, within the pacemaker 20, not only to the timing and control circuit 34 but also to the memory 30.

Coupled to the pulse generator circuit 32 is at least one conventional pacing lead 40 (although more pacing leads may be used if needed, as would be the case for a patient receiving dual-chamber pacing therapy). The pacing lead 40 is used to deliver pacing pulses provided by the pulse generator 32 to the patient's heart 42. In addition, the pacing lead 40 senses the natural rhythm of the heart 42 (e.g., the patient's intracardiac electrogram, i.e. IEGM) and presents a signal indicative thereof to the timing and control circuit 34. The ability to sense the natural rhythm of the heart 42 enables the pacemaker 20 to operate in a demand mode, in which delivery of a pacing pulse is inhibited by the timing and control circuit 34 when a naturally occurring cardiac contraction is sensed during the escape interval following a preceding contraction.

Although the following description assumes that the pacemaker 20 operates in a demand mode, it should be understood that other implementations are possible. Also, demand mode may be a telemetrically programmable feature, allowing the pacemaker 20 to be switched into and out of demand mode when desired by a physician of other clinician.

In order to regulate the rate at which the pacemaker 20 delivers pacing pulses to the heart 42, the processor 26 provides a rate control signal to the timing and control circuit 34. The rate control signal provided by the processor 26 preferably adjusts the escape interval used by the timing and control circuit 34, which has the effect of changing the maintained heart rate. Increasing (i.e., lengthening) the escape interval decreases the maintained heart rate, because the pacemaker 20 gives the heart 42 more time to contract on its own before the next pacing pulse is delivered. Decreasing (i.e., shortening) the escape interval has the opposite effect. It will be appreciated, however, by those of skill in the art that the precise manner in which the processor controls the pacing rate is not critical for purposes of the present invention and that alternatives to the control process just described will be apparent.

In general, the stimulation device contemplated herein includes a pulse generator for generating pacing pulses to the heart; at least one sensor, such as an activity, minute ventilation sensor, or contractility sensor (e.g., QT interval, etc.) for sensing a diurnally varying physiological parameter indicative of the patient's circadian rhythm and for generating sensor signals corresponding thereto; a memory for storing information relevant to pacing parameters that will be varied diurnally, such as the various predetermined (either by the programmer or the pacemaker) heart rates described further below; and a processor for controlling the rate of the pacing pulses.

The processor, preferably includes means such as a microprocessor, for processing the sensor signals generated by the sensor. For example, activity levels measured by the sensor are preferably processed into activity variance data, a parameter which has been shown to vary diurnally, as described further below. The processor is capable of selecting sensor measurements for storage, as a histogram, in the memory means and deriving the appropriate circadian base rate for the patient according to the method described herein. It will be appreciated by those of skill in the art that microprocessors, solid state machines and combinations thereof may be employed to perform the methods described herein and are likewise contemplated herein.

In general, the improved method contemplated herein comprises deriving a circadian base rate by manipulating the target daytime and nighttime values of a pacing parameter and the normal circadian variations of a physiological parameter (e.g., activity variance, minute ventilation, QT interval, ventricular gradient, etc.).

Thus, in this embodiment, the method comprises the steps of: providing a predetermined daytime and nighttime target values of a desired pacing parameter (e.g., base rate); measuring, over a period of time, a physiological parameter which varies diurnally; determining daytime and nighttime values for the physiological parameter; and deriving a linear function based on the daytime and nighttime values for the pacing parameter, and daytime and nighttime values of the physiological parameter to determine the circadian varying pacing parameter (e.g., base rate).

It will further be appreciated that the pacemaker 20 illustrated in FIG. 1 is exemplary of pacemakers that may be used with the present invention. Any programmable, rate-responsive pacemaker, or ICD with rate-responsive pacing capabilities, that has a sensor capable of sensing circadian biorhythms may be programmed to adjust base pacing rates in accordance with the present invention, as described further below.

While the first embodiment, discussed below, will address the patient's need to diurnally change heart rate, this is for teaching purposes only and is only one example of a pacing parameter which can benefit from the present invention. Other pacing parameters and a set of generalized equations will also follow the exemplary embodiments.

The first embodiment of the present invention contemplated herein includes an improved method for controlling the pacemaker, which method employs an algorithm, programmable into the pacemaker's processor, that automatically sets up the circadian change in pacing rate. The control mechanism or algorithm is simple to implement and easy to program, in part because a physician (or the pacemaker) need only provide at least two diurnal target values to establish a desired range over which the device should operate. For example, in the first embodiment, a target daytime and a target nighttime base rate is provided (or automatically determined by the pacemaker) in order for the algorithm to proceed. The result is a programmed circadian base rate that very closely matches the normal sinus rate of a healthy heart. That is, the circadian base rate histogram very closely matches the normal sinus rate histogram.

In order to demonstrate the effectiveness of the algorithm contemplated for use herein, eleven normal volunteers (age 20 to 57 years) wore a modified Holter monitor for 24 hours. The Holter recorded the surface ECG, a raw accelerometer signal from a "taped-on" pacemaker and the transcutaneous impedance signal measured non-invasively over the left thoracic area. The subjects engaged in a series of prescribed, as well as normal daily activities. A program extracted the 24 hour sinus rate histogram and trend from the ECG; activity variance histogram from the activity signal; and minute ventilation histogram from the impedance signal. Activity variance was measured as a running average of the absolute difference between activity levels measured every 30 seconds. The sinus rate histogram was modeled as a sum of several Gaussian distributions. As described further below, this model provided the mean daytime and mean nighttime heart rates of the subjects, which is the only information that would need to be provided by the clinician.

Figure 2:
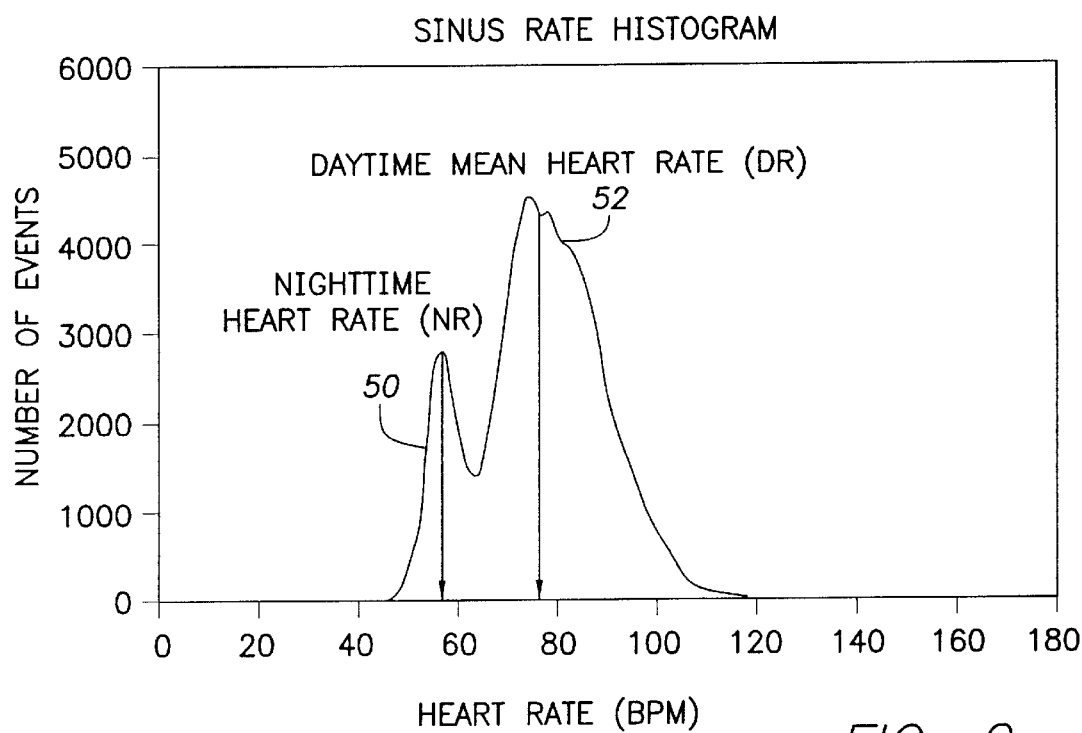
FIG. 2 is a graph of an exemplary sinus rate histogram with mean daytime and mean nighttime heart rates identified.

FIG. 2 is a graph of a typical sinus rate histogram as determined from the sum of the several Gaussian distributions. As seen in FIG. 2, this sinus rate histogram model provides two dominant distributions 50, 52, the means of which distributions correspond to mean nighttime and mean daytime heart rates. As stated above, it will typically be the physician, or other clinician, who determines the target daytime and target nighttime heart rates and programs that information into the pacemaker. Such target daytime and nighttime rates, when not directly selected by the physician, will preferably be selected based upon individual factors such as the patient's height, weight, age and gender. However, any technique known to those of skill in the art for making such determinations may be used. From the sinus rate histogram of the subjects, illustrated in FIG. 2, the mean daytime rate is 77 bpm and the mean nighttime rate is 58 bpm. Having determined the target daytime and nighttime heart rates, the invention next develops a histogram based upon the measurements of the physiological sensor.

Figure 3:
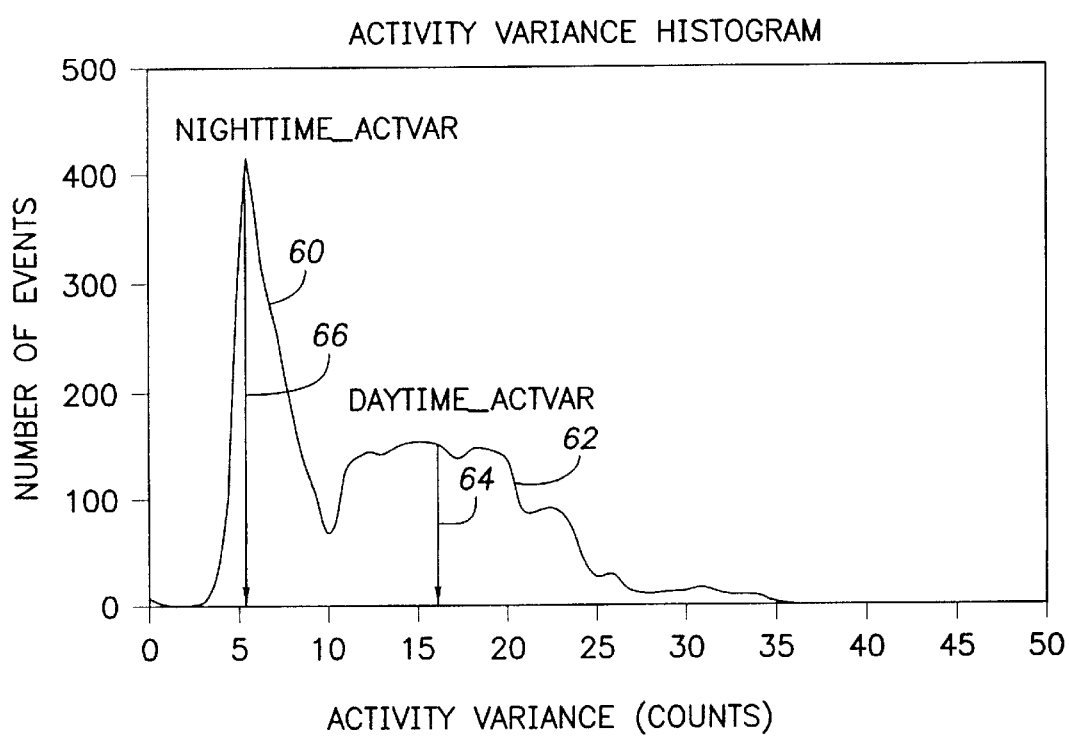
FIG. 3 is a graph of an exemplary activity variance histogram, developed in accordance with the present invention and identifying mean daytime and mean nighttime activity variances.

In a preferred embodiment, the sensor is an activity sensor, the diurnally varying physiological parameter is activity variance, and thus, an activity variance histogram is developed. FIG. 3 shows an activity variance histogram developed from data obtained from the eleven-subject trial described above. For the purposes of this preferred embodiment, activity variance levels were measured every 30 seconds for a 24-hour period. The activity variance histogram was then developed therefrom. As with the sinus rate histogram, the activity variance histogram has two distinct distributions 60, 62. Unlike the sinus rate histogram, however, one distribution 62 is highly variable. This is the daytime activity variance, which correlates to the variable levels of typical daytime activity. In contrast, the other distinct distribution shows little variation, corresponding to the minimal variations in activity during sleep.

From the activity variance histogram, the pacemaker calculates the mean daytime activity variances (daytime_ActVar) 64, and the mean nighttime (nighttime_ActVar) activity variance 66. While the mean values have been chosen, this is also for illustrative purposes and other statistical methods for determining a characteristic value could be used, such as determining the midpoint, mode, central value, etc. These calculations are then used to generate a transfer function that applies the diurnal variations of the activity variance parameter to the daytime and nighttime target values for base rate to arrive at a circadian base rate, as shown below in Eqs. 1–3.

The simplest transfer function is a linear function (see Eq. 3, below). The base rate slope (BR_slope), and an Intersection determine this linear function uniquely. Base rate_slope (BR_slope) and Intersection are evaluated automatically and updated periodically according to the following equations:

$$BR\_slope=(DR-NR)/(daytime\_ActVar-nighttime\_ActVar) \quad \text{Eq. 1:}$$

$$Intersection=NR-(BR\_slope*nighttime\_ActVar) \quad \text{Eq. 2:}$$

where DR and NR are the target daytime and nighttime base rates, respectively; and where daytime_ActVar and nighttime_ActVar are the daytime and nighttime mean values of the diurnally-varying physiological parameter (i.e., activity variance).

Using a linear relationship, and determining a current value of the activity variance, ActVar(t), one can determine a current circadian base rate, CBR(t) for the patient according to the following equation:

$$CBR(t)=BR\_slope*ActVar(t)+Intersection. \quad \text{Eq. 3:}$$

Thus, once the daytime and nighttime base rates are programmed in by the physician or clinician, the system will automatically determine the naturally occurring circadian variations in the base rate corresponding the diurnal variations as measured by some physiological parameter, in this case, activity variance. That is, variations in the physiological parameter which are centered about the mean daytime value, will result in similar variations in base rate about the predetermined daytime base rate. Likewise, variations in the physiological parameter which are centered about the mean nighttime value, will result in variations in base rate about the predetermined nighttime base rate.

Figure 4:
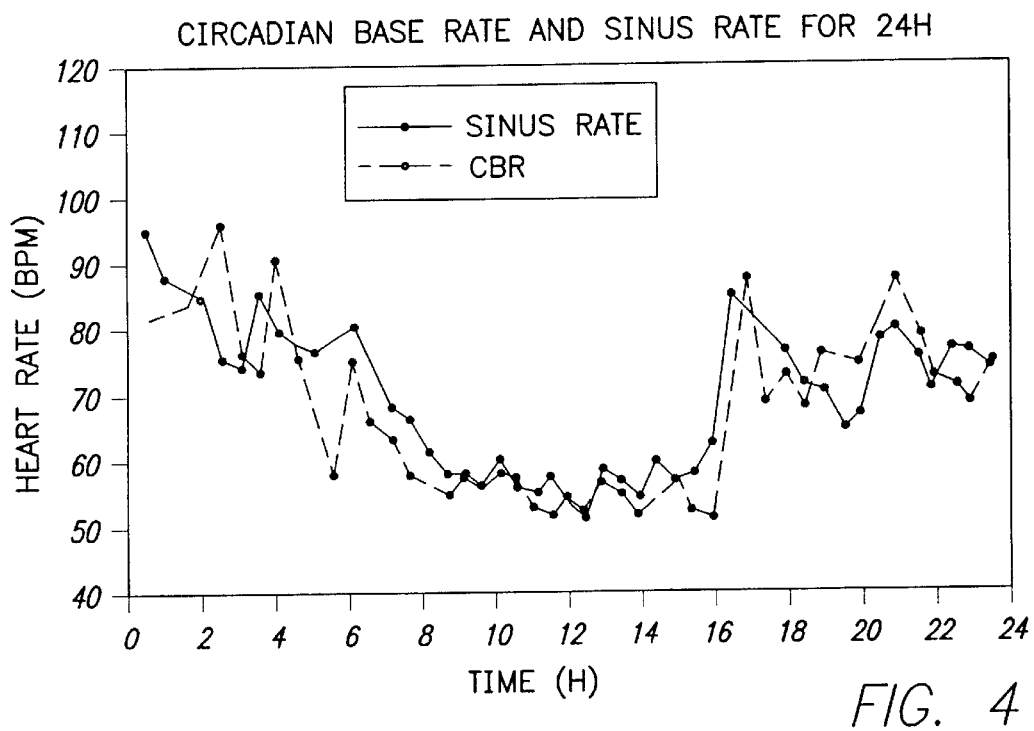
FIG. 4 is a graph comparing a patient's measured sinus rate to the patient's corresponding circadian base rate over a 24 hour period, wherein the circadian base rate has been adjusted, according to the present invention, by the activity variance measurements illustrated in FIG. 3.

FIG. 4 illustrates a typical daily response of the circadian base rate as measured using the above equations, Eq. 1, 2 and 3. Also shown in this graph is the 24-hour sinus rate, demonstrating that such an activity variance-based circadian base rate very closely mimics normal sinus rate in healthy adults. For the study presently referenced, the error between sinus rate and circadian base rate, for all subjects, when averaged for every 30 minutes, was 7.6±1.7%.

Figure 5:
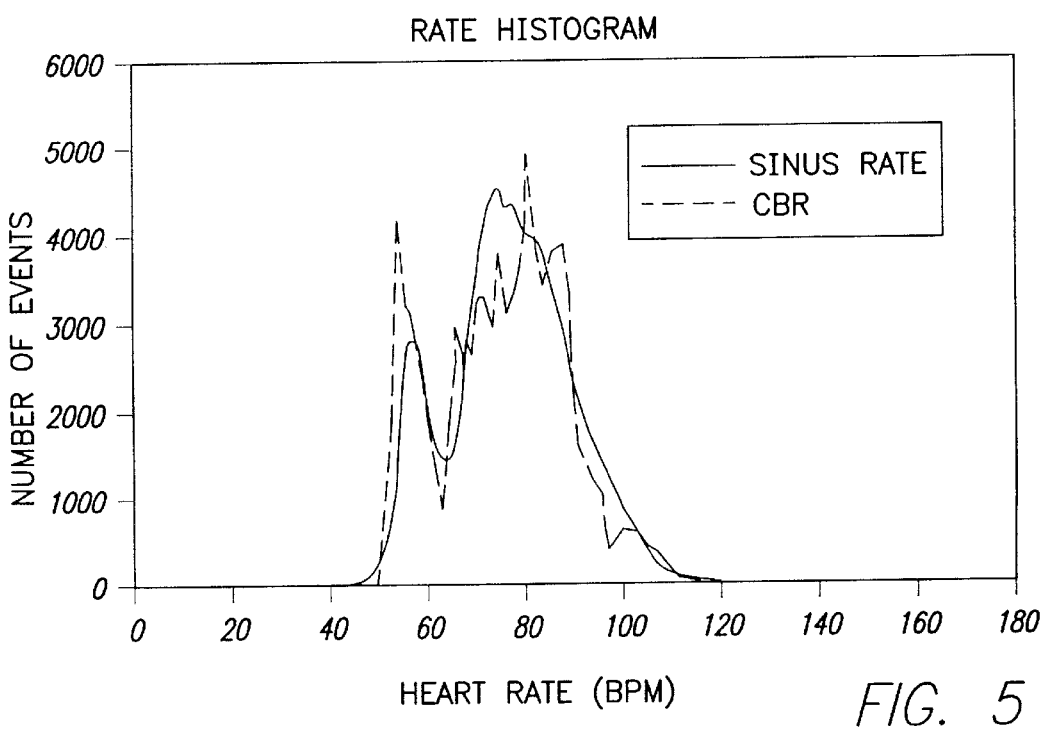
FIG. 5 is a graph comparing a patient's circadian base rate histogram of the circadian base rate illustrated in FIG. 4 to the sinus rate histogram of the same patient.

FIG. 5 compares the activity variance-based circadian base rate histogram with the sinus rate histogram, illustrating the very close relationship between the activity variance and sinus rate.

Figure 6:
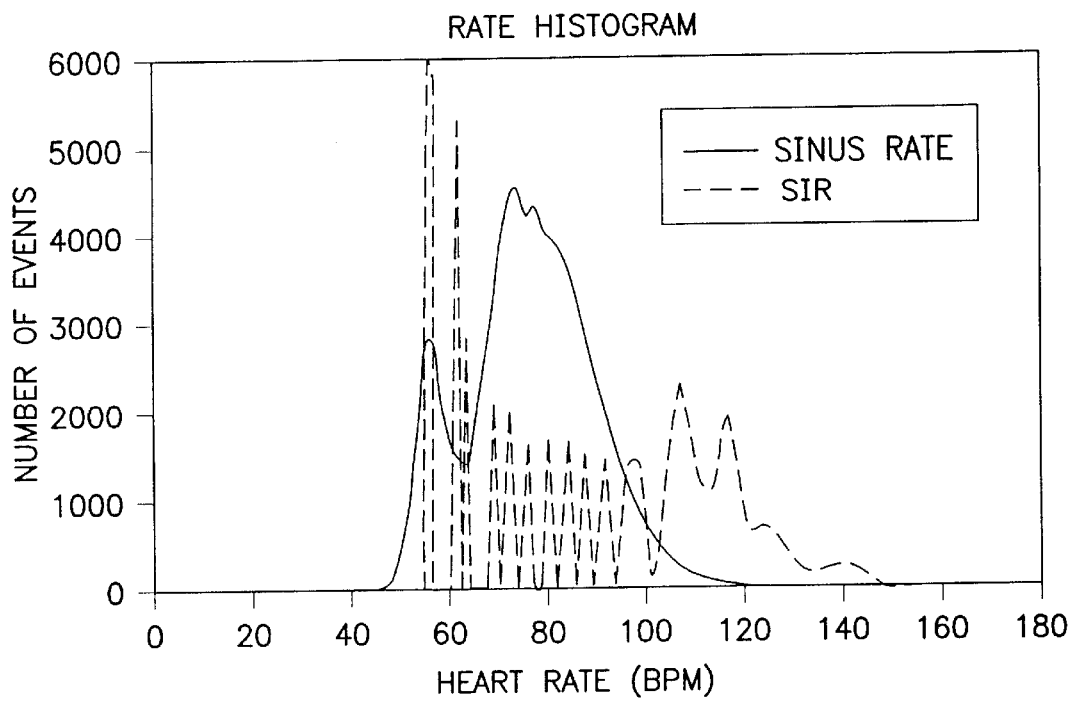
FIG. 6 is a graph of a patient's sensor indicated rate (SIR) histogram, obtained by a prior art activity variance method, compared to the patient's sinus rate histogram.

In contrast, FIG. 6 is a graph of a sensor-indicated rate (SIR) histogram, obtained by an ordinary activity algorithm, compared to the sinus rate histogram. As can be seen in FIG. 6, there is no useful correlation between the activity-based sensor-indicated rate and the sinus rate histograms.

In an alternative embodiment of the invention, minute ventilation, rather than activity variance, is used to determine the appropriate circadian base rate.

It is well known that minute ventilation is determined by measuring respiration rate and tidal volume thought the use of an impedance sensor. While the circuitry to measure minute ventilation (i.e., rate detector and impedance) is often referred to collectively as a minute ventilation sensor, it is important to note that minute ventilation measurements are used directly as the diurnally varying physiological parameter.

Figure 7:
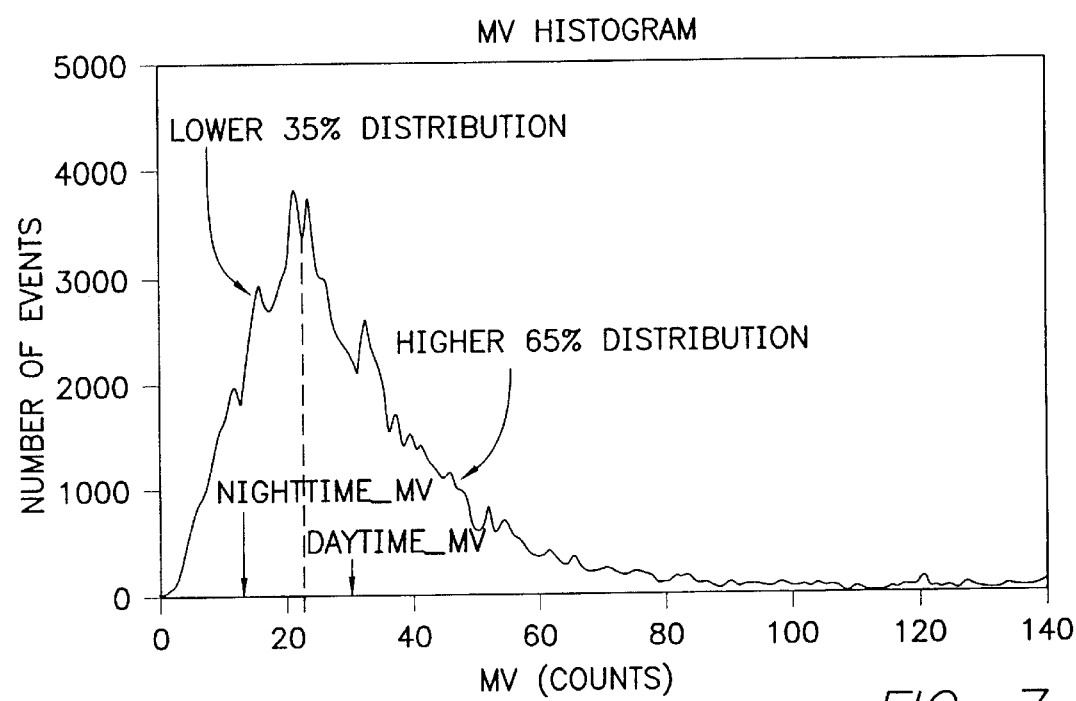
FIG. 7 is a graph of an exemplary minute ventilation histogram, developed in accordance with the present invention and identifying mean daytime and mean nighttime minute ventilations.

In this case, again the physician need only program a desired or target daytime and nighttime rates for the patient. Minute ventilation data is then processed by the pacemaker to develop a minute ventilation (MV) histogram. A typical minute ventilation histogram, developed from the eleven-subject study described above, is illustrated in FIG. 7. The minute ventilation histogram curve, shown in FIG. 7, is divided into two areas by the pacemaker: one constituting the lower 35% of the distribution and the other constituting the upper 65% thereof. It was determined that most subjects' nighttime minute ventilation distribution belonged to the lower area; whereas, their daytime minute ventilation distribution fell into the higher area.

Other sensors that may be used instead of minute ventilation to produce a histogram similar to the one shown in FIG. 7 include contractility sensors, such as QT interval or ventricular gradient (also referred to as Post-ventricular depolarization interval), stroke volume, or any sensor that has diurnal variations that can be quantified by a histogram and partitioned into daytime and nighttime values.

Thus, as shown in Eqs. 4–6, the algorithm controlling the pacemaker automatically calculates a mean minute ventilation for the lower, nighttime, area (nighttime_MV) and a mean minute ventilation for the higher, daytime, area (daytime_MV), from the minute ventilation (MV) histogram. These calculations are then used to evaluate a transfer function that converts a current minute ventilation value, MV(t), to a current value for a circadian base rate, CBR(t). The simplest transfer function is a linear function again using a base rate slope and an Intersection. Base rate slope (BR_slope) and Intersection are evaluated automatically and updated periodically according to the following equations:

$$BR\_slope=(DR-NR)/(daytime\_MV-nighttime\_MV) \qquad \text{Eq. 4:}$$

$$Intersection=NR-BR\_slope*nighttime\_MV \qquad \text{Eq. 5:}$$

where DR and NR are the target daytime and nighttime base rates, respectively; and where daytime_MV and nighttime_MV are the daytime and nighttime mean values of the diurnally-varying physiological parameter (i.e., minute ventilation).

Using a linear relationship, and determining a current value of minute ventilation, MV(t), one can determine a current circadian base rate, CBR(t) for the patient according to the following equation:

$$CBR(t)=BR\_slope*MV(t)+Intersection. \qquad \text{Eq. 6:}$$

Figure 8:
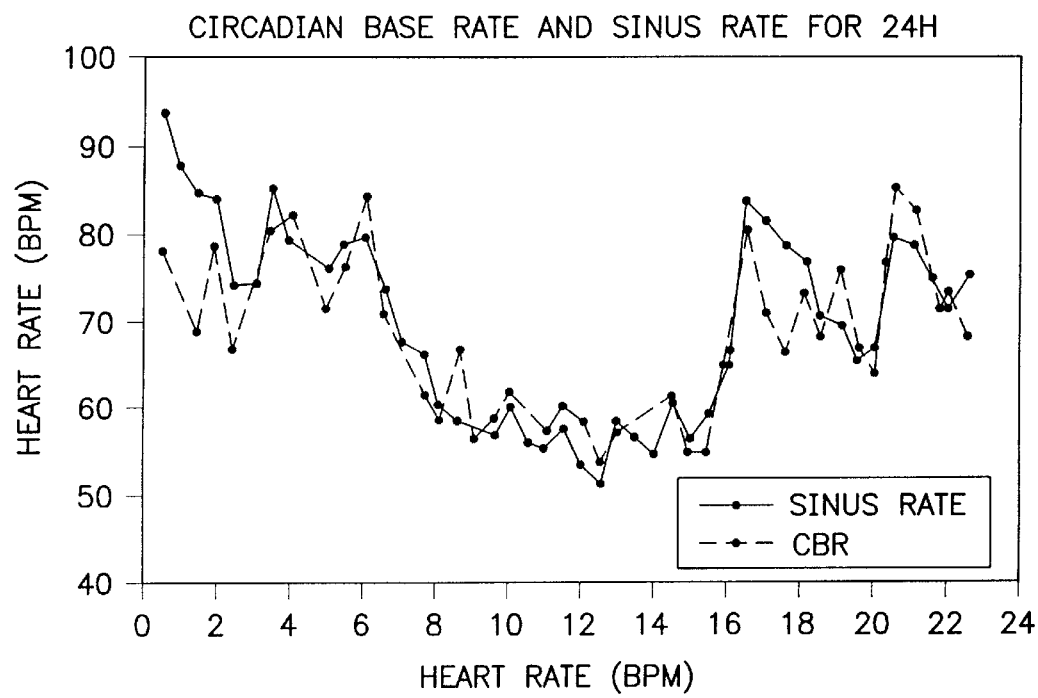
FIG. 8 is a graph comparing a patient's measured sinus rate to the patient's corresponding circadian base rate over a 24 hour period, wherein the circadian base rate has been adjusted, according to the present invention, by the minute ventilation measurements illustrated in FIG. 7.
Figure 9:
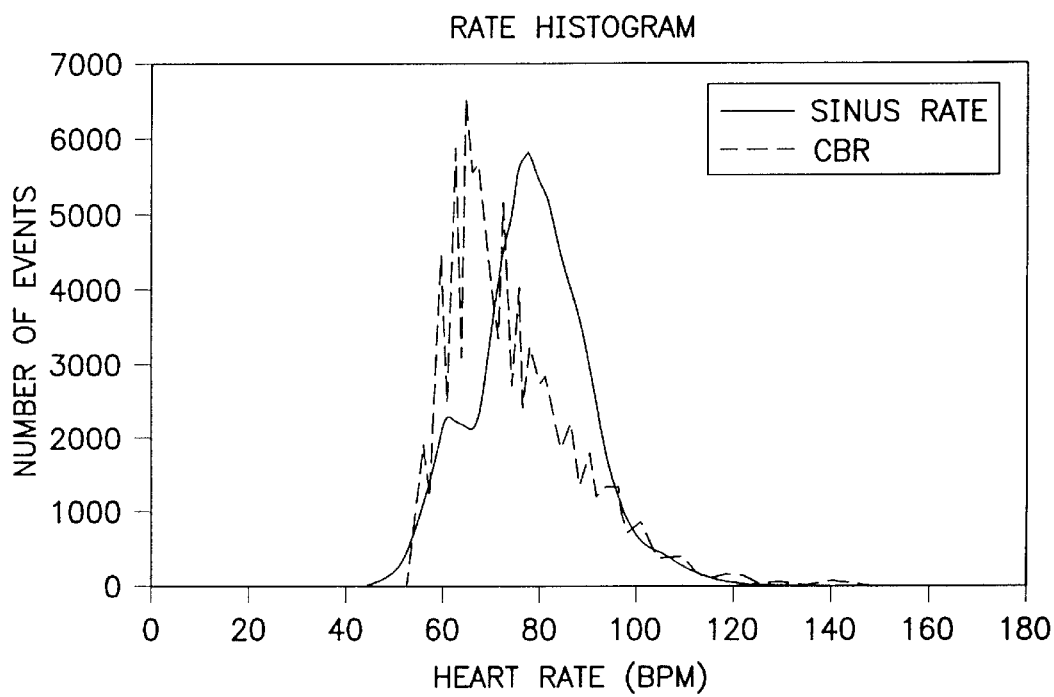
FIG. 9 is a graph comparing a patient's circadian base rate histogram of the circadian base rate illustrated in FIG. 8 to the sinus rate histogram of the same patient.

Illustrated in FIG. 8 is a typical daily response of the minute ventilation-based circadian base rate, calculated using Eqs. 4, 5 and 6. The sinus rate is also graphed thereon. Again, the correlation between the two rates, over a 24-hour period, is striking. When averaged for every 30 minutes for all eleven subjects tested, the error between sinus rate and minute ventilation-based circadian base rate was only 8.1±1.8%. Further, FIG. 9 illustrates that the minute ventilation-based circadian base rate histogram matches the corresponding sinus rate histogram.

Thus, it is seen that use of physiological sensor measurements, according to the present invention, to first determine base rate slope and an Intersection, followed by use of those equations to determine the circadian base rate, results in a rate that very closely mimics the natural diurnal fluctuations of the normal sinus rate. Further contemplated herein, and as will be appreciated by those of skill in the art given the disclosures herein, is the use of both activity variance and minute ventilation measurements to set the circadian base rate. This may be done for example, by averaging the two circadian base rates, that is the circadian base rate determined from Eqs. 1 and 2 averaged with that provided by Eqs. 3 and 4, to provide a single minimum pacing rate or the minute ventilation-based circadian base rate may be used to verify the accuracy of the activity variance-based circadian base rate or vice versa, by comparison of one with the other.

While the embodiment described above is directed toward adjusting the base rate for circadian variations, the present invention can be adapted to adjust a variety of pacing parameters to have circadian variations. These pacing parameters include, but are not limited to, AV Delay, the threshold for Automatic Mode Switching algorithms, tachycardia thresholds, or any pacing parameter which could benefit from diurnal variations.

Consequently, the equations to compute a current value for a Circadian-Based value, CBV(t), for the desired pacing parameter could be rewritten in a more general format as:

$$CBV(t)=slope*Physio(t)+Y-Intercept$$

wherein:

$$Slope = \frac{daytime\_parameter - nighttime\_parameter}{daytime\_Physio - nighttime\_Physio}$$

Y-Intercept=nighttime_parameter−(slope*nighttime_Physio)

where Physio(t) represents the current value of the physiological sensor;

where daytime_parameter and nighttime_parameter are the target daytime and nighttime pacing parameters which need circadian variation, respectively; and where daytime_Physio and nighttime_Physio are the daytime and nighttime mean values of the diurnally-varying physiological parameter.

Although the present invention has been discussed in detail with reference to certain preferred embodiments thereof, other embodiments are possible and likewise contemplated as included herein. Therefore, the spirit and scope of the appended claims should not be limited to the description of the preferred embodiments contained herein.

What is claimed is:

1. In an implantable stimulation device, a method of automatically adjusting a desired pacing parameter to mimic natural diurnal fluctuations, the device having a sensor capable of sensing a physiological parameter having circadian variations, the method comprising:

determining a daytime and a nighttime value for the desired pacing parameter;

sensing the physiological parameter for a predetermined period of time;

deriving, from the sensed physiological parameter, an average daytime and an average nighttime value for the physiological parameter;

determining a circadian-based function based on the daytime and the nighttime value of the desired pacing parameter, and based on the average daytime and nighttime value of the physiological parameter;

determining a current value for the physiological parameter;

determining a current circadian-based value for the desired pacing parameter based on the circadian-based function and the current value of the physiological parameter, whereby the desired pacing parameter changes diurnally as the physiological parameter changes; and adjusting the desired pacing parameter according to the circadian-based value.

2. The method, according to claim 1, wherein the desired pacing parameter includes a desired daytime and nighttime pacing rate value, wherein the step of determining the circadian-based function comprises the step of:

determining the circadian-based function based on the desired daytime and nighttime pacing rate value and based on the average daytime and nighttime value of the physiological parameter.

3. The method, according to claim 1, wherein the desired pacing parameter includes a desired daytime and nighttime AV Delay value, wherein the step of determining the circadian-based function comprises the step of:

determining the circadian-based function based on a desired daytime and nighttime AV Delay value and based on the average daytime and nighttime value of the physiological parameter.

4. The method, according to claim 1, wherein the desired pacing parameter includes a desired daytime and nighttime diurnally-varying threshold value, wherein the step of determining the circadian-based function comprises the step of:
  determining a circadian-based function based on the desired daytime and nighttime diurnally-varying threshold value and based on the average daytime and nighttime value of the physiological parameter.

5. The method, according to claim 1, wherein the desired pacing parameter includes a desired daytime and nighttime defibrillation amplitude value, wherein the step of determining the circadian-based function comprises the step of:
  determining a circadian-based function based on the desired daytime and nighttime defibrillation amplitude value and based on the average daytime and nighttime value of the physiological parameter.

6. The method, according to claim 1, wherein the desired pacing parameter includes a desired daytime and nighttime defibrillation therapy mode value, wherein the step of determining the circadian-based function comprises the step of:
  determining a circadian-based function based on the desired daytime and nighttime defibrillation therapy mode value and based on the average daytime and nighttime value of the physiological parameter, whereby aggressiveness of therapy is diurnally varied.

7. The method, according to claim 1, wherein the sensing of the physiological parameter is performed by an activity sensor ad wherein the step of deriving the average daytime and nighttime values for the physiological parameter comprises the steps of:
  developing a histogram based on the activity sensor;
  dividing the histogram into two distributions representative of primarily daytime and nighttime activity variances, respectively; and
  determining the average daytime and average nighttime activity variances corresponding to the two distributions.

8. The method, according to claim 1, wherein the sensing of the physiological parameter is performed by a minute ventilation sensor and wherein the step of deriving the average daytime and nighttime values for the physiological parameter comprises the steps of:
  developing a histogram from the minute ventilation sensor;
  dividing the histogram into two distributions representative of primarily daytime and nighttime minute ventilation values, respectively; and
  determining the average daytime and nighttime minute ventilation values corresponding to the two distributions.

9. The method, according to claim 8, wherein the step of dividing the histogram into two distributions comprises the step of:
  dividing the histogram into a first distribution comprising approximately a lower 35% of the distribution and a second distribution comprising approximately an upper 65% of the distribution.

10. The method, according to claim 1, wherein the sensing of the physiological parameter is performed by a QT interval sensor and wherein the step of deriving the average daytime and nighttime values for the physiological parameter comprises the steps of:
  developing a histogram based on the QT interval sensor;
  dividing the histogram into two distributions representative of primarily daytime and nighttime activity variances, respectively; and
  determining the average daytime and nighttime QT interval values corresponding to the two distributions.

11. The method, according to claim 10, wherein the step of dividing the histogram into two distributions comprises the step of:
  dividing the histogram into a first distribution comprising approximately a lower 35% of the distribution and a second distribution comprising approximately an upper 65% of the distribution.

12. The method, according to claim 1, wherein the step of determining a current circadian-based value, CBV(t), for the desired pacing parameter based on the current value of the physiological parameter, Physio(t), comprises the step of calculating:

$$CBV(t) = slope \ast Physio(t) + Y\text{-Intercept}$$

wherein:

$$Slope = \frac{daytime\_parameter - nighttime\_parameter}{daytime\_Physio - nighttime\_Physio}$$

$$Y\text{-Intercept} = nighttime\_parameter - (slope \ast nighttime\_Physio)]$$

wherein the predetermined daytime and nighttime values of the desired pacing parameters are defined as daytime_parameter and nighttime_parameter, respectively; and
  wherein the average daytime and nighttime values of the physiological parameter are defined as daytime_Physio and nighttime_Physio, respectively.

13. In an implantable programmable rate-responsive stimulation device, a method of automatically determining a circadian base pacing rate wherein the circadian base pacing rate mimics natural diurnal fluctuations in heart rate, the device having a sensor capable of sensing a physiological parameter having circadian variations, the method comprising:
  determining a daytime and a nighttime value for the pacing rate;
  sensing the physiological parameter for a predetermined period of time;
  determining an average daytime and an average nighttime value for the sensed physiological parameter;
  determining a base rate slope based on the daytime and nighttime values of the pacing rate and the average daytime and nighttime values for the physiological parameter;
  determining a current value for the physiological parameter;
  determining a current circadian-based value for the pacing rate based on the base rate slope and the current value of the physiological parameter; and
  adjusting the pacing rate according to the current circadian-based value.

14. The method, according to claim 13, wherein the sensor is an activity sensor which senses activity levels, wherein the physiological parameter is the activity levels, and wherein the step of deriving the average daytime and nighttime values in the physiological parameter comprises the step of:
  determining the average daytime and nighttime activity values based on the activity levels sensed over the predetermined time period.

15. The method, according to claim 14, wherein the step of determining the average daytime and nighttime activity values comprises the steps of:

developing a histogram based on the sensed activity levels;

dividing the histogram into two distributions representative of primarily daytime and nighttime activity levels; and determining from the divided histogram the variance between the average daytime and nighttime activity values of the physiological parameter.

16. The method, according to claim 15, wherein the step of developing a histogram comprises the step of:

determining activity variance as an average of the absolute difference between regularly sensed activity levels and developing an activity variance histogram therefrom.

17. The method, according to claim 16, wherein the step of determining activity variance comprises the step of:

determining an average of the absolute difference between activity levels sensed about every 30 seconds.

18. The method, according to claim 13, wherein the step of calculating the base rate slope (BR_slope) comprises the step of calculating the relationship:

$$BR\_Slope = \frac{daytime\_baserate - nighttime\_baserate}{daytime\_Physio - nighttime\_Physio}$$

wherein the daytime baserate and nighttime baserate are the desired daytime and nighttime base rates and the daytime Physio and nighttime Physio are the daytime and nighttime mean values of the diurnally-varying physiological parameter.

19. The method, according to claim 18, wherein the step of determining a current value for the circadian base rate, CBR(t), as a function of the physiological parameter, Physio (t), comprises the step of determining:

$$CBR(t) = BR\_Slope * Physio(t) + Y\text{-Intercept}$$

wherein the Y-Intercept is calculated according to the relationship:

$$Y\_Intercept = nighttime\_baserate - BR\_Slope * nighttime\ Physio.$$

20. The method, according to claim 13, wherein the sensor is a minute ventilation sensor, the physiological parameter having circadian variations is minute ventilation, and wherein the step of deriving the average daytime and nighttime values in the physiological parameter comprises the steps of:

sensing minute ventilation values over a predetermined period of time;

generating a histogram based on the minute ventilation values; and determining the average daytime and nighttime minute ventilation based on the minute ventilation histogram sensed over the predetermined time period.

21. The method, according to claim 20, wherein the steps of sensing the physiological parameter and generating a histogram additionally comprises the step of:

dividing the histogram into two distributions representative of primarily daytime and primarily nighttime pacing needs, the histogram comprising a lower distribution of approximately 35% or less, representative of nighttime pacing rates and an upper distribution of approximately 65% or more, representative of daytime pacing rates.

22. The method according to claim 13, wherein the sensing step comprises sensing at least two physiological parameters, and wherein the step of deriving the current circadian based-value for the pacing rate comprises the steps of:

deriving a first circadian base rate related to a first of the at least two sensed physiological parameters;

deriving a second circadian base rate related to a second of the at least two sensed physiological parameters; and deriving a final circadian base rate as an average of the first and second circadian base rates.

23. The method according to claim 13, wherein the sensing step comprises sensing at least two physiological parameters, one designated a primary parameter and the other designated a secondary parameter, wherein the step of deriving the circadian base rate further comprises the steps of:

deriving a primary circadian base rate from the primary physiological parameter;

deriving a secondary circadian base rate from the secondary physiological parameter;

comparing the primary circadian base rate to the secondary circadian base rate; and determining a final circadian base rate equivalent to the primary circadian base rate if the difference between the primary circadian base rate and the secondary circadian base rate is not statistically significant.

24. A cardiac stimulation device for automatically adjusting at least one pacing parameter to mimic natural diurnal fluctuations, comprising:

a pulse generator for generating stimulation pulses to the heart;

a sensor capable of sensing a physiological parameter having circadian variations for a predetermined period of time;

means for determining a desired daytime and nighttime target value for a desired pacing parameter;

a processor, coupled to the pulse generator, the sensor, and the determining means, for automatically adjusting the desired pacing parameter about the desired target values to mimic natural circadian fluctuations, the processor including:

means for deriving at least an average daytime and an average nighttime value in the physiological parameter;

means for determining a current value for the physiological parameter; and means for determining a current circadian-based value for the desired pacing parameter based on the desired daytime and nighttime target values of the desired pacing parameter, and the average daytime and nighttime values of the physiological parameter, and the current value of the physiological parameter;

whereby the current circadian-based value of the desired pacing parameter changes diurnally as the value of the physiological parameter changes.

25. The stimulation device, according to claim 24, wherein the desired pacing parameter is a base pacing rate.

26. The stimulation device, according to claim 24, wherein the desired pacing parameter is an AV Delay.

27. The stimulation device, according to claim 24, wherein the desired pacing parameter is a diurnally-varying threshold.

28. The stimulation device, according to claim 24, wherein the desired pacing parameter is a defibrillation output amplitude.

29. The stimulation device, according to claim 24, wherein the desired pacing parameter is a defibrillation therapy mode.

30. The stimulation device, according to claim 24, wherein the sensor is an activity sensor and wherein the means for deriving the average daytime and nighttime values in the physiological parameter comprises:
- means for developing a histogram from the activity sensor;
- means for dividing the histogram into two distributions representative of primarily daytime and nighttime activity variances, respectively; and
- means for determining from the divided histogram the average daytime and average nighttime activity variances.

31. The stimulation device, according to claim 24, wherein the sensor is a minute ventilation sensor ad wherein the means for deriving the average daytime and nighttime values in the physiological parameter comprises:
- means for developing a histogram from the minute ventilation sensor;
- means for dividing the histogram into two distributions representative of primarily daytime and nighttime minute ventilation values, respectively; and
- means for determining from the divided histogram the average daytime and average nighttime minute ventilation values.

32. The stimulation device, according to claim 31, wherein the means for dividing the histogram into two distributions comprises:
- means for dividing the histogram into a first distribution comprising approximately a lower 35% of the distribution and a second distribution comprising approximately an upper 65% of the distribution.

33. The stimulation device, according to claim 24, wherein the sensor comprises a QT interval sensor and wherein the means for deriving the average daytime and the average nighttime variance in the physiological parameter comprises:
- means for developing a histogram from the QT interval sensor;
- means for dividing the histogram into two distributions representative of primarily daytime and nighttime QT interval values, respectively; and
- means for determining from the divided histogram the average daytime and average nighttime QT interval values.

34. The stimulation device, according to claim 33, wherein the means for dividing the histogram into two distributions comprises:
- means for dividing the histogram into a first distribution comprising approximately a lower 35% of the distribution and a second distribution comprising approximately an upper 65% of the distribution.

35. The stimulation device, according to claim 24, wherein the means for determining the circadian-based value comprises:
- means for determining a linear function based on the desired daytime and nighttime target values of the desired pacing parameter and based on the average daytime and nighttime values of the physiological parameter.

36. The stimulation device, according to claim 35, wherein the means for determining a current circadian-based value, CBV(t), for the desired pacing parameter based on the linear function and the current value, Physio(t), of the physiological parameter comprises means for calculating the following relationship:

$$CBV(t) = slope * Physio(t) + Y\text{-Intercept}$$

wherein:

$$Slope = \frac{daytime\_parameter - nighttime\_parameter}{daytime\_Physio - nighttime\_Physio}$$

$$Y\text{-Intercept} = nighttime\_parameter - (slope * nighttime\_Physio)$$

wherein the desired daytime and nighttime target values of the desired pacing parameter are defined as daytime_parameter and nighttime_parameter, respectively; and wherein the mean daytime and nighttime values of the physiological parameter are defined as daytime_Physio and nighttime_Physio, respectively.

37. A cardiac stimulation device for automatically adjusting at least one pacing parameter to mimic natural diurnal fluctuations, comprising:
- a pulse generator that generates stimulation pulses to the heart;
- a sensor that senses a physiological parameter having diurnal variations and generates sensor signals thereof;
- a memory that stores at least two predetermined values of the pacing parameter, the values corresponding to a diurnal rhythm; and
- a processor, coupled to the pulse generator, the sensor and the memory, that controls the at least one pacing parameter, the processor further determines diurnally varying values for the at least one pacing parameter based upon a function of the diurnal variations of the physiological parameter and corresponding values of the pacing parameter, and the processor triggers the pulse generator to generate stimulation pulses in accordance with the diurnally varying values of the pacing parameter.

38. The stimulation device, according to claim 37, wherein the sensor measures activity levels and wherein the physiological parameter corresponds to activity levels.

39. The stimulation device, according to claim 37, wherein the sensor measures minute ventilation levels and wherein the physiological parameter corresponds to minute ventilation levels.

40. The stimulation device, according to claim 37, wherein the sensor measures QT intervals and wherein the physiological parameter corresponds to QT intervals.

41. The stimulation device, according to claim 37, wherein the pacing parameter comprises a base rate.

42. The stimulation device, according to claim 37, wherein the pacing parameter comprises an AV Delay.

43. The stimulation device, according to claim 37, wherein the pacing parameter comprises a pacing threshold.

44. The stimulation device, according to claim 37, wherein the predetermined values correspond to a daytime and a nighttime value of the pacing parameter and wherein the diurnally varying value of the pacing parameter is based upon a function of the diurnal variations of the physiological parameter and the daytime and nighttime values of the pacing parameter.

45. In an implantable stimulation device, a method of automatically adjusting a desired pacing parameter to mimic natural diurnal fluctuations, the device having a sensor capable of sensing a physiological parameter having circadian variations, the method comprising:

sensing a physiological parameter having diurnal variations;

determining at least two diurnally varying values of the pacing parameter which correspond to a diurnal range of operation;

determining diurnally varying values for the at least one pacing parameter based upon a function of the diurnal variations of the physiological parameter and the corresponding diurnally varying values of the pacing parameter; and triggering the device to generate stimulation pulses in accordance with the circadian varying values of the pacing parameter.

46. The method, according to claim 45, wherein the step of determining at least two values of the pacing parameter comprises the step of:

determining at least a daytime and a nighttime value of the pacing parameter.

47. The method of claim 45 wherein the at least two values of the pacing parameter correspond to a daytime and a nighttime range of operation and the determining diurnally varying values step determines the values based upon the diurnal variations of the physiological parameter and the daytime and nighttime values of the pacing parameter.

* * * * *